(12) United States Patent
Kim et al.

(10) Patent No.: US 12,421,221 B2
(45) Date of Patent: Sep. 23, 2025

(54) HETEROCYCLIC-SUBSTITUTED PYRIMIDINE DERIVATIVE EXHIBITING CANCER CELL GROWTH INHIBITORY EFFECT, AND PHARMACEUTICAL COMPOSITION CONTAINING SAME

(71) Applicant: ONCOBIX CO., LTD., Yongin-si (KR)

(72) Inventors: Sung-Eun Kim, Seoul (KR); Sunho Lee, Seoul (KR); Rengasamy Rajesh, Suwon-si (KR); Yong Hyub Lee, Goyang-si (KR); Sung Tak Hong, Seoul (KR)

(73) Assignee: ONCOBIX CO., LTD., Yongin-si (KR)

( * ) Notice: Subject to any disclaimer, the term of this patent is extended or adjusted under 35 U.S.C. 154(b) by 989 days.

(21) Appl. No.: 17/601,790

(22) PCT Filed: Oct. 8, 2020

(86) PCT No.: PCT/KR2020/013779
§ 371 (c)(1),
(2) Date: Oct. 6, 2021

(87) PCT Pub. No.: WO2021/085888
PCT Pub. Date: May 6, 2021

(65) Prior Publication Data
US 2022/0204492 A1    Jun. 30, 2022

(30) Foreign Application Priority Data

Oct. 31, 2019 (KR) .......... 10-2019-0137489

(51) Int. Cl.
| | | |
|---|---|---|
| C07D 413/14 | (2006.01) |
| C07D 403/14 | (2006.01) |
| C07D 417/14 | (2006.01) |
| C07D 487/10 | (2006.01) |
| C07D 491/107 | (2006.01) |

(52) U.S. Cl.
CPC ......... *C07D 413/14* (2013.01); *C07D 403/14* (2013.01); *C07D 417/14* (2013.01); *C07D 487/10* (2013.01); *C07D 491/107* (2013.01)

(58) Field of Classification Search
CPC .. C07D 403/12; C07D 487/10; C07D 498/10; A61K 31/5377; A61K 31/541; A61K 31/506
See application file for complete search history.

(56) References Cited

U.S. PATENT DOCUMENTS

| | | | |
|---|---|---|---|
| 10,059,688 B2 | 8/2018 | Hu et al. | |
| 11,351,168 B1 | 6/2022 | Singh et al. | |
| 2006/0247241 A1 | 11/2006 | Garcia-Echeverria et al. | |
| 2010/0029610 A1 | 2/2010 | Singh et al. | |
| 2012/0172385 A1 | 7/2012 | Harrison et al. | |
| 2012/0202776 A1 | 8/2012 | Wang et al. | |
| 2014/0031351 A1 | 1/2014 | Breslin et al. | |
| 2014/0128387 A1 | 5/2014 | Wang et al. | |
| 2017/0226065 A1 | 8/2017 | Shönbrunn et al. | |
| 2018/0044323 A1 | 2/2018 | Lv et al. | |
| 2020/0179384 A1 | 6/2020 | Lee et al. | |
| 2021/0147439 A1 | 5/2021 | Kim et al. | |
| 2021/0267997 A1 | 9/2021 | Choi et al. | |
| 2023/0219986 A1* | 7/2023 | Deng ................. C07F 9/65583 514/81 |

FOREIGN PATENT DOCUMENTS

| | | |
|---|---|---|
| CN | 108047204 A | 5/2018 |
| EP | 3392245 A1 | 10/2018 |
| JP | 2016-525509 A | 8/2016 |
| KR | 10-2005-0109987 A | 11/2005 |
| KR | 10-2011-0025224 A | 3/2011 |
| KR | 10-2018-0098167 A | 9/2018 |
| KR | 10-2018-0135781 A | 12/2018 |
| KR | 10-2019-0067699 A | 6/2019 |
| RU | 2 632 907 C2 | 10/2017 |
| RU | 2 675 850 C2 | 12/2018 |
| WO | 2004/080980 A1 | 9/2004 |
| WO | 2009/143389 A1 | 11/2009 |
| WO | 2009/158571 A1 | 12/2009 |
| WO | 2012/125603 A1 | 9/2012 |
| WO | 2019/190259 A1 | 10/2019 |

OTHER PUBLICATIONS

V.G. Belikov, Farmatsevticheskaya Khimiya [Pharmaceutical Chemistry], 2007, pp. 27-29 (14 pages total).
G. Dyson, et al., Khimiya Sinteticheskikh Lekarstvennukh Veshchestv [Chemistry of Synthetic Drugs], 1964, pp. 12-19 (21 pages total).
Russian Office Action issued Jan. 29, 2024 in Application No. 2021134202.
Extended European Search Report dated Sep. 21, 2023 issued by the European Patent Office in EP application No. 20880791.7.
Pao, W., et al, "New driver mutations in non-small-cell lung cancer" The Lancet Oncol., 2011, vol. 12, pp. 175-180 (6 pages total).
Yasuda, H., et al, "Preclinical rationale for use of the clinically-available multitargeted tyrosine kinase inhibitor crizotinib in ROS1 translocated lung cancer", Journal of Thoracic Oncology, Jul. 2021, vol. 7, No. 7, pp. 1086-1090 (9 pages total).
Shaw, A. T., et al., "ALK in Lung Cancer: Past, Present, and Future", Journal of Clinical Oncology, vol. 31, No. 8, Mar. 10, 2013, pp. 1105-1111 (7 pages total).

(Continued)

*Primary Examiner* — Jeffrey H Murray
*Assistant Examiner* — Madeline E Braun
(74) *Attorney, Agent, or Firm* — Sughrue Mion, PLLC

(57) ABSTRACT

The present invention provides a novel compound represented by Chemical Formula 1 or a salt thereof and a pharmaceutical composition for treating lung cancer containing same. A pyrimidine derivative compound represented by Chemical Formula 1 effectively inhibits the growth of cancer cells with an ALK mutation and an EGFR mutation, thereby being effectively usable in the treatment of lung cancer.

8 Claims, No Drawings
Specification includes a Sequence Listing.

(56) References Cited

OTHER PUBLICATIONS

Paez, J. G., "EGFR Mutations in Lung Cancer: Correlation with Clinical Response to Gefitinib Therapy", Science, vol. 304, Jun. 4, 2004 (5676), pp. 1497-1500 (4 pages total).
Lynch, T. J., et al., "Activating Mutations in the Epidermal Growth Factor Receptor Underlying Responsiveness of Non-Small-Cell Lung Cancer to Gefitinib", New England Journal of Medicine, vol. 350, No. 21, May 20, 2004, pp. 2129-2139 (11 pages total).
Yu, H. A., et al., "Analysis of Tumor Specimens at the Time of Acquired Resistance to EGFR-TKI Therapy in 155 Patients with EGFR-Mutant Lung Cancers", Clinical Cancer Research, vol. 19, No. 8, 2013, pp. 2240-2247 (9 pages total).
Jiang, T., et al., "A consensus on the role of osimertinib in non-small cell lung cancer from the AME Lung Cancer Collaborative Group", Journal of Thoracic Disease, vol. 10, No. 7, Jul. 10, 2018, pp. 3909-3921 (13 pages total).
Wang, S., et al., "EGFR C797S mutation mediates resistance to third-generation inhibitors in T790M-positive non-small cell lung cancer", Journal of Hematology & Oncology, vol. 9, No. 59, 2016 (5 pages total).
Thress, K. S., et al., "Acquired EGFR C797S mutation mediates resistance to AZD9291 in non-small cell lung cancer harboring EGFR T790M", Nature Medicine, vol. 21, No. 6, May 4, 2015 (5 pages total).
Wang, Y., et al., "Clinical analysis by next-generation sequencing for NSCLC patients with MET amplification resistant to osimertinib", Lung Cancer, vol. 118, 2018, pp. 105-110 (24 pages total).
Qiuxiang Ou, et al., "Investigating novel resistance mechanisms to third generation EGFR TKI osimertinib in non-small cell lung cancer patients using next generation sequencing.", Journal of Clinical Oncology, vol. 35, No. 15, abstract, 2572, May 20, 2017 (2 pages total).
Zofia Piotrowska, et al., "MET amplification (amp) as a resistance mechanism to osimertinib", Journal of Clinical Oncology, vol. 35, No. 15, abstract, 9020, May 20, 2017 (2 pages total).
Jang, J., et al., "Discovery of a potent dual ALK and EGFR T790M inhibitor", European Journal of Medicinal Chemistry, vol. 136, pp. 497-510, 2017 (50 pages total).
Wenfeng Gou, et al., "ZX-29, a novel ALK inhibitor, induces apoptosis via ER stress in ALK rearrangement NSCLC cells and overcomes cell resistance caused by an ALK mutation", BBA—Molecular Cell Research, vol. 1867, 118712, Mar. 26, 2020 (11 pages total).
International Search Report dated Jan. 15, 2021 from the International Searching Authority in International Application No. PCT/KR2020/013779.
Written Opinion dated Jan. 15, 2021 from the International Searching Authority in International Application No. PCT/KR2020/013779.

* cited by examiner

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: synthetic construct

<400> SEQUENCE: 1

Lys Lys Lys Gly Gln Glu Glu Glu Tyr Val Phe Ile Glu
1               5                   10

HETEROCYCLIC-SUBSTITUTED PYRIMIDINE DERIVATIVE EXHIBITING CANCER CELL GROWTH INHIBITORY EFFECT, AND PHARMACEUTICAL COMPOSITION CONTAINING SAME

CROSS REFERENCE TO RELATED APPLICATIONS

This application is a National Stage of International Application No. PCT/KR2020/013779 filed Oct. 8, 2020, claiming priority based on Korean Patent Application No. 10-2019-0137489 filed Oct. 31, 2019, the entire contents of which are incorporated herein by reference.

INCORPORATION BY REFERENCE OF SEQUENCE LISTING

The content of the electronically submitted sequence listing, file name: Q268410 Sequence Listing.txt; size: 662 Bites; and date of creation: May 12, 2025, filed herewith, is incorporated herein by reference in its entirety.

TECHNICAL FIELD

The present invention relates to a novel heterocyclic-substituted pyrimidine derivative to effectively inhibit cancer cell growth and a pharmaceutical composition containing the same.

BACKGROUND ART

Non-small cell lung cancer (NSCLC) is a disease that has recently very high prevalence and mortality of cancer-related diseases in the world. The NSCLC is mainly caused by mutations, overexpression, and the like of a tyrosine kinase enzyme, and anticancer agents for treating the NSCLC have been developed by targeting active inhibition of these enzymes. The NSCLC, which is mainly caused in East Asia, including Korea, has many cases of epidermal growth factor receptor (EGFR) gene mutations, and drugs with relatively low toxicity and a good treating effect have been developed.

In addition, the NSCLC is caused by expression, rearrangement, etc. of various tumor genes, which correspond to anaplastic lymphoma kinase (ALK), KRAS, ROS1, etc. (LANCET ONCOL 2011; 12 (2): 175-80.).

In some NSCLC patients, ALK abnormality (EML4-alk transfusion, etc.) is observed, and various tyrosine kinase inhibitors (TKIs) and the like are clinically used to treat the cancer. ALK-positive NSCLC is caused by ALK-EML4 fusion, and while the ALK gene, which has been normally latent by the fusion of the two genes, rapidly increases the growth rate of the cells, the cells receiving this signal are rapidly transited to cancer cells. As a representative therapeutic drug for patients with the mutation, crizotinib was approved as a multi-targeted anticancer therapeutic agent in US FDA in 2011. These drugs have been used for treatment of metastatic, ALK positive NSCLC, etc. through activity inhibition on MET, ALK, ROS1, and the like. As a clinical study result of crizotinib, patients with lung cancer with an adenocarcinoma tissue form participated mainly and 46% thereof were Asian. The crizotinib had very excellent efficacy such as about 65% of tumor response rate, 7.7 months (3 months of chemotherapeutic group) of progress-free survival, etc., and the most commonly reported abnormal response was abnormalities of visual field, diarrhea, vomiting, edema, nausea, or the like (J Thorac Oncol 2012; 7 (7): 1086-90.).

The crizotinib is used to inevitably cause resistance, and has been mainly reported to cause secondary mutation occurrence (about 30%) in an ALK kinase domain, the amplification of an ALK fusion mutant gene, and activation of a bypass signaling process, etc. There are very various mutations, but among the mutations, there are secondary mutations including L1196M and G1269A, L1196M which is located at the most frequent gate-keeper residue to induce the ALK binding interference with crizotinib, etc. (J Clin Oncol 2013; 31 (8): 1105-11.).

In a kinase region of the epidermal growth factor receptor (EGFR), activating mutations del119 and L858R have been found as carcinogen genes in some patients with NSCLC, and gefitnib, erlotinib and the like as low molecular EGFR inhibitors for treating the lung cancer have been used as therapeutic agents (Science 2004, 304:1497-500; and New England Journal of Medicine 2004, 350:2129-39).

When gefitnib and erlotinib are used as therapeutic agents to the patients with NSCLC in which the EGFR activating mutations are confirmed, in most patients, the resistance to drugs is expressed within one year (Clinical Cancer Research 2013; 19:2240-7). A T790M mutation ratio of the epidermal growth factor receptor during such a resistance mechanism is observed at up to 60%. Accordingly, a $3^{rd}$ generation EGFR inhibitor that targets a T790M mutation EGFR in lung cancer has been developed. As a representative drug, there are osimertinib, lasertinib, and the like, and these drugs target the T790M mutation and exhibit relatively low toxicity to be clinically used for treatment of NSCLC (J Thorac Dis. 2018 July; 10 (7): 3909-3921).

However, it has been reported that the drug resistance of the $3^{rd}$ generation EGFR inhibitor is inevitable, and as a main resistance mechanism, C797S mutation, MET amplification, and the like have been reported (J Hematol Oncol. Jul. 22, 2016; 9 (1): 59; Nature Medicine 2015, 21, 560-562; Lung Cancer 2018, 118, 105-110; and ASCO2017 abstract 2572, 9020). It has been reported that the C797S mutation and the MET amplification are separately found, but simultaneously found.

It has been reported that in the non-small cell lung cancer (NSCLC) caused by the ALK mutation or the EGFR mutation (or both), all of the secondary mutations that inhibit the binding force of the kinase-drug affect intracellular sub signaling as a main resistance mechanism (Eur Med Chem. 2017 Aug. 18; 136:497-510.). Even though various ALK and EGFR inhibitors have been continuously developed, inhibitors inhibiting two types of kinases together have been very slow developed. Therefore, the development of drugs that effectively inhibit the growth of cancer cells of ALK mutation or EGFR mutation, which is the main drug resistance mechanism described above, has been required.

PRIOR ART DOCUMENT

Patent Document (Patent Document 1) PCT Patent Publication No. WO/2009/143389A1

DISCLOSURE

Technical Problem

The present inventors have made an effort to develop a novel compound that effectively inhibits ALK mutation cancer and EGFR mutation cancer. As a result, a novel heterocyclic-substituted pyrimidine derivative was found to be effective in cancer treatment. In particular, the novel heterocyclic-substituted pyrimidine derivative was confirmed to express an excellent effect on the treatment of lung cancer.

Therefore, an object of the present invention is to provide a novel heterocyclic-substituted pyrimidine derivative having an effect on cancer treatment.

Another object of the present invention is to provide a pharmaceutical composition for treating lung cancer including the heterocyclic-substituted pyrimidine derivative.

Yet another object of the present invention is to provide a pharmaceutical composition for treating lung cancer expressing an ALK mutation or EGFR mutation even in lung cancer.

Still another object of the present invention is to provide a pharmaceutical composition for treating lung cancer expressing an ALK mutation and EGFR mutation even in lung cancer.

Technical Solution

In order to achieve the above object, the present invention provides a compound represented by the following Chemical Formula 1 or a salt thereof:

[Chemical Formula 1]

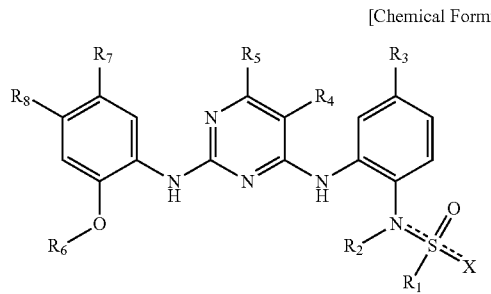

X is oxygen, an amine group substituted or unsubstituted with an alkyl group of C1 to C4 or an alkyl group of C1 to C4, $R_1$ is an alkyl group of C1 to C4, a cycloalkyl group of C3 to C6, $CF_3$, or a dimethylamine group, $R_2$ is H or an alkyl group of C1 to C4, $R_3$ is hydrogen or a halogen group, $R_4$ is hydrogen, a halogen group, CN, $CF_3$, an alkyl group of C1 to C4, or an amino carbonyl group, $R_5$ is hydrogen or an alkyl group of C1 to C4, $R_6$ is hydrogen or an alkyl group of C1 to C4, $R_7$ is a heterocyclic compound substituted or unsubstituted with an alkyl group of C1 to C4 and consisting of one or more nitrogen atoms and 2 to 10 carbon atoms, $R_8$ is an aliphatic heterocyclic compound substituted or unsubstituted with an alkyl group of C1 to C4 and consisting of one or more hetero atoms selected from nitrogen atoms, oxygen atoms, and sulfur atoms and 2 to 10 carbon atoms; or a $N^1,N^1,N^2$-tri (C1 to C4 alkyl)ethylene diamine group, wherein when X is oxygen, X forms a double bond with S, and S forms a single bond with N, and when X is an amine group substituted or unsubstituted with an alkyl group of C1 to C4 or an alkyl group of C1 to C4, X forms a single bond with S, and S forms a double bond with N.

The present invention also provides a compound represented by Chemical Formula 1 used for treating lung cancer or a salt thereof.

Further, the present invention provides a pharmaceutical composition for treating lung cancer containing the compound represented by Chemical Formula 1 or a pharmaceutically acceptable salt thereof and a pharmaceutically acceptable carrier as active ingredients.

Further, the present invention provides a method for treating animals having lung cancer comprising administering the compound represented by Chemical Formula 1 to animals in an effective dose.

Further, the present invention provides use for treating lung cancer of the compound represented by Chemical Formula 1.

Advantageous Effects

According to the present invention, the novel heterocyclic-substituted pyrimidine derivative compound provides an excellent effect on cancer treatment.

Further, according to the present invention, the pharmaceutical composition for treating lung cancer including the heterocyclic-substituted pyrimidine derivative compound provides excellent activity to the treatment of lung cancer, particularly, effectively inhibits the growth of ALK mutation cancer cells and EGRE mutation cancer cells.

BEST MODE

Hereinafter, exemplary embodiments of the present invention will be described in detail. However, the exemplary embodiments are illustrative, and thus, the present invention is not limited thereto, and the present invention will be only defined by the scope of the claims to be described below. Further, despite configurations to implement the present invention, a detailed description will be omitted for configurations capable of being easily implemented by those skilled in the art from known techniques.

Hereinafter, unless otherwise described, the term "the compound of the present invention" or "the compound of Chemical Formula 1" is used as a concept that includes both a compound itself and its salts.

In this specification, the term "alkyl group" refers to a linear and branched hydrocarbon group having a specified number of carbon atoms. The alkyl group may be, for example, methyl, ethyl, n-propyl, i-propyl, n-butyl, s-butyl, i-butyl, t-butyl, etc.

In this specification, the term "alkylsulfonyl" means alkyl $—S(O_2)—$. Here, alkyl is defined above.

The present invention relates to a compound represented by the following Chemical Formula 1 or a salt thereof:

A compound represented by Chemical Formula 1 below or a salt thereof:

[Chemical Formula 1]

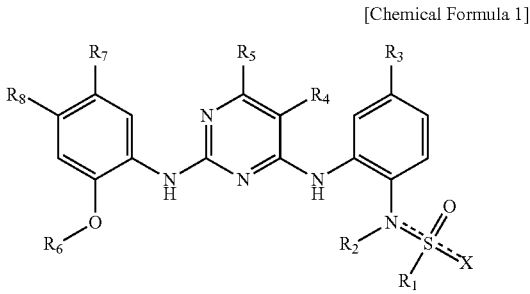

X is oxygen, an amine group substituted or unsubstituted with an alkyl group of C1 to C4 or an alkyl group of C1 to C4, $R_1$ is an alkyl group of C1 to C4, a cycloalkyl group of C3 to C6, CF3, or a dimethylamine group, $R_2$ is H or an alkyl group of C1 to C4, $R_3$ is hydrogen or a halogen group, $R_4$ is hydrogen, a halogen group, CN, $CF_3$, an alkyl group of C1 to C4, or an amino carbonyl group, $R_5$ is hydrogen or an alkyl group of C1 to C4, $R_6$ is hydrogen or an alkyl group of C1 to C4, $R_7$ is a heterocyclic compound substituted or unsubstituted with an alkyl group of C1 to C4 and consisting of one or more nitrogen atoms and 2 to 10 carbon atoms, $R_8$ is an aliphatic heterocyclic compound substituted or unsubstituted with an alkyl group of C1 to C4 and consisting of one or more hetero atoms selected from nitrogen atoms, oxygen atoms, and sulfur atoms and 2 to 10 carbon atoms; or a $N^1,N^1,N^2$-tri (C1 to C4 alkyl)ethylene diamine group, wherein when X is oxygen, X forms a double bond with S, and S forms a single bond with N, and when X is an amine group substituted or unsubstituted with an alkyl group of C1 to C4 or an alkyl group of C1 to C4, X forms a single bond with S, and S forms a double bond with N.

Further, with respect to $R_7$ and $R_8$, the $R_7$ may be a heterocyclic compound substituted or unsubstituted with an alkyl group of C1 to C4 and consisting of one or more nitrogen atoms and 2 to 10 carbon atoms, and the $R_8$ may be an aliphatic heterocyclic compound substituted or unsubstituted with an alkyl group of C1 to C4 and consisting of two or more hetero atoms selected from nitrogen atoms, oxygen atoms, and sulfur atoms and 2 to 10 carbon atoms; or a $N^1,N^1,N^2$-tri (C1 to C4 alkyl)ethylene diamine group.

Further, with respect to $R_7$ and $R_8$, the $R_7$ may be a pyrazolyl group substituted or unsubstituted with a C1 to C4 alkyl group, an imidazolyl group substituted or unsubstituted with a C1 to C4 alkyl group, or a triazolyl group substituted or unsubstituted with a C1 to C4 alkyl group, and the $R_8$ may be a morpholinyl group substituted or unsubstituted with a C1 to C4 alkyl group, a thiomorpholinyl group substituted or unsubstituted with a C1 to C4 alkyl group, piperazinyl substituted or unsubstituted with a C1 to C4 alkyl group, a diazaspiro compound of C5 to C10 substituted or unsubstituted with a C1 to C4 alkyl group, an oxoazaspiro compound of C5 to C10 substituted or unsubstituted with a C1 to C4 alkyl group, a thioazaspiro compound of C5 to C10 substituted or unsubstituted with a C1 to C4 alkyl group, or a $N^1,N^1,N^2$-tri (C1 to C4 alkyl)ethylene diamine group.

The $R_7$ is selected from the following compounds, and

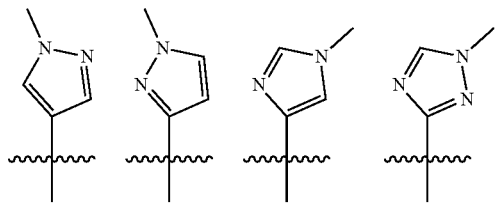

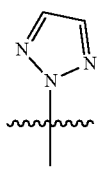

the $R_8$ may be selected from the following compounds:

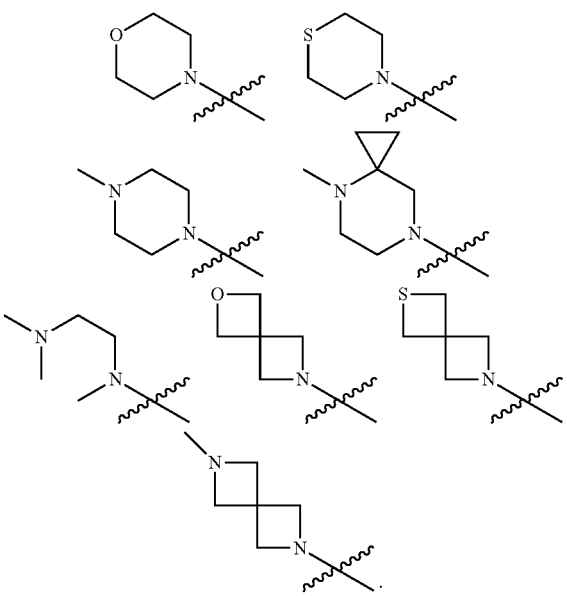

In the compound represented by Chemical Formula 1 of the present invention or a salt thereof, X is oxygen, $R_1$ is an alkyl group of C1 to C4, $R_2$ is H or an alkyl group of C1 to C4, $R_3$ is hydrogen or a halogen group, $R_4$ is hydrogen or a halogen group, $R_5$ is hydrogen or an alkyl group of C1 to C4, $R_6$ is an alkyl group of C1 to C4, $R_7$ is selected from the following compounds, and

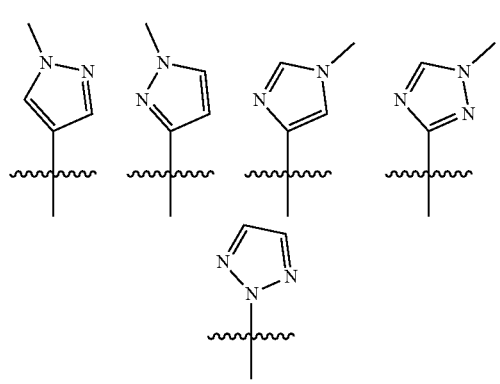

$R_8$ may be selected from the following compounds:

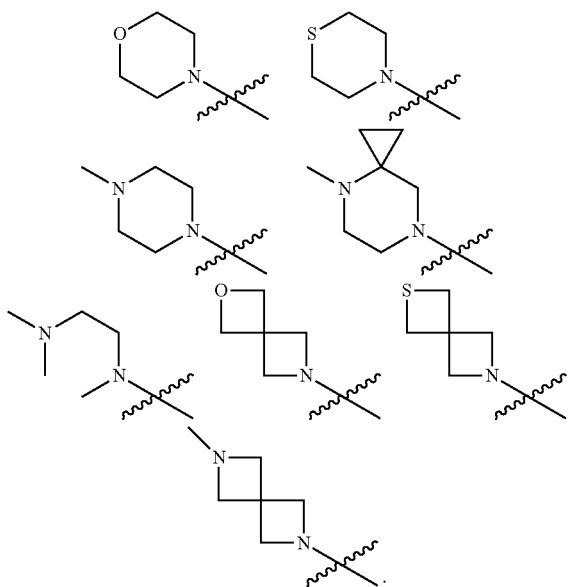

Specifically, the compound represented by Chemical Formula 1 above may be selected from the following compounds:

N-(2-((5-chloro-2-((2-methoxy-5-(1-methyl-1H-pyrazol-4-yl)-4-morpholinophenyl)amino)pyrimidine-4-yl)amino)phenyl)-N-methylmethanesulfonamide (Chemical Formula 1), N-(2-((5-chloro-2-((2-methoxy-5-(1-methyl-1H-pyrazol-4-yl)-4-morpholinophenyl)amino)pyrimidine-4-yl)amino)phenyl)methanesulfonamide (Chemical Formula 2), N-(2-((5-chloro-2-((2-methoxy-5-(1-methyl-1H-pyrazol-4-yl)-4-thiomorpholinophenyl)amino)pyrimidine-4-yl)amino)phenyl)-N-methoxymethanesulfonamide (Chemical Formula 3), N-(2-((5-chloro-2-((2-methoxy-5-(1-methyl-1H-pyrazol-4-yl)-4-(4-methylpiperazine-1-yl)phenyl)amino)pyrimidine-4-yl)amino)phenyl)-N-methoxymethanesulfonamide (Chemical Formula 4), N-(2-((5-chloro-2-((2-methoxy-5-(1-methyl-1H-pyrazol-4-yl)-4-(2-oxa-6-azaspiro[3.3]heptane-6-yl)phenyl)amino)pyrimidine-4-yl)amino)phenyl)-N-methylmethanesulfonamide (Chemical Formula 5), N-(2-((5-chloro-2-((2-methoxy-5-(1-methyl-1H-pyrazol-4-yl)-4-(6-methyl-2,6-diazaspiro[3.3]heptane-2-yl)phenyl)amino)pyrimidine-4-yl)amino)phenyl)-N-methylmethanesulfonamide (Chemical Formula 6), N-(2-((5-chloro-2-((2-methoxy-5-(1-methyl-1H-pyrazol-4-yl)-4-thiomorpholinophenyl)amino)pyrimidine-4-yl)amino)phenyl)methanesulfonamide (Chemical Formula 7), N-(2-((5-chloro-2-((2-methoxy-5-(1-methyl-1H-pyrazol-4-yl)-4-(4-methylpiperazine-1-yl)phenyl)amino)pyrimidine-4-yl)amino)phenyl)methanesulfonamide (Chemical Formula 8), N-(2-((5-chloro-2-((2-methoxy-5-(1-methyl-1H-pyrazol-4-yl)-4-(2-oxa-6-azaspiro[3.3]heptane-6-yl)phenyl)amino)pyrimidine-4-yl)amino)phenyl)methanesulfonamide (Chemical Formula 9), and N-(2-((5-chloro-2-((2-methoxy-5-(1-methyl-1H-pyrazol-4-yl)-4-(6-methyl-2,6-diazaspiro[3.3]heptane-2-yl)phenyl)amino)pyrimidine-4-yl)amino)phenyl)methanesulfonamide (Chemical Formula 10).

In the present invention, the salt may be a salt form induced by at least one acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, benzoic acid, hydroxybenzoic acid, phenyl acetic acid, cinnamic acid, salicylic acid, methanesulfonic acid, ethanesulfonic acid, benzene sulfonic acid, toluene sulfonic acid, etc.

Further, the present invention relates to a pharmaceutical composition for treating lung cancer containing the compound represented by Chemical Formula 1 or a pharmaceutically acceptable salt thereof and a pharmaceutically acceptable carrier as active ingredients.

The lung cancer may be ALK mutation or epidermal growth factor receptor (EGFR) mutation expression lung cancer.

The lung cancer may be non-small cell lung cancer.

The pharmaceutical composition of the present invention may be used for treating, particularly, lung cancer, and may be effectively used for treatment of lung cancer with ALK mutation or EGFR mutation cancer cells even in lung cancer.

The pharmaceutical composition of the present invention has an effect of simultaneously having inhibitory activity to ALK (L1196M or EML4-AlK amplification mutation) and EGFR (C797S).

In the present invention, the compound represented by Chemical Formula 1 may be used in a salt form induced by inorganic acids or organic acids, and for example, may be used in a salt form induced by at least one acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, benzoic acid, hydroxybenzoic acid, phenyl acetic acid, cinnamic acid, salicylic acid, methanesulfonic acid, ethanesulfonic acid, benzene sulfonic acid, toluene sulfonic acid, etc.

Further, the present invention relates to a compound represented by Chemical Formula 1 used for treating lung cancer or a salt thereof.

Further, the present invention relates to a method for treating animals having lung cancer comprising administering the compound represented by Chemical Formula 1 to animals in an effective dose.

Further, the present invention relates to use of treating lung cancer, particularly non-small cell lung cancer of the compound represented by Chemical Formula 1.

The animal may be human, and the lung cancer may be lung cancer having ALK mutation or EGFR mutation cancer cells.

The ALK mutation may be L1196M, and EML4-AlK fusion mutations, and the EGFR mutation may be one or more mutations selected from L858R, T790M, del19, and C797S.

The pharmaceutical composition of the present invention may be formulated according to a conventional method, and may be prepared in various oral administration forms such as tablets, pills, powders, capsules, syrups, emulsions, microemulsions, etc., or in parenteral administration forms such as intravenous injection, subcutaneous injection, intramuscular injection, abdominal injection, percutaneous injection, and direct tissue injection.

When the pharmaceutical composition of the present invention is prepared in the form of oral formulations, as the pharmaceutically acceptable carrier, known ingredients in the art may be used without limitation unless interrupted to activity expression of the active ingredients.

Examples of the carrier include excipients, diluents, disintegrants, binders, lubricants, surfactants, emulsifiers, suspending agents, diluents, etc., but are not limited thereto.

When the pharmaceutical composition of the present invention is prepared in the form of injections, as the/ pharmaceutically acceptable carrier, known ingredients in the art may be used without limitation unless interrupted to activity expression of the active ingredients.

Specifically, the pharmaceutically acceptable carrier may include, for example, water, saline, a glucose aqueous solution, a sugar-like aqueous solution, alcohol, glycol, ether (e.g., polyethylene glycol 400), oil, fatty acid, fatty acid ester, glyceride, a surfactant, a suspension, an emulsifier, etc., but is not limited thereto.

The dosage of the pharmaceutical composition of the present invention may be determined by considering the age, gender, and condition of a patient, the absorption of active ingredients in the body, inactivity and combined drugs, and may be injected in 0.0001 mg/kg (body weight) to 100 mg/kg (body weight) once based on the compound of Chemical Formula 1. The administration number is suitably about once to three times a day.

[Modes for the Invention]

Hereinafter, the present invention will be described in more detail through Examples. These Examples are to explain the present invention in more detail, and it will be apparent to those skilled in the art that the scope of the present invention is not limited by these Examples in accordance with the gist of the present invention.

Synthesis Method of Compounds Represented by Chemical Formula 1

Compounds represented by the following Chemical Formula 1 according to the present invention may be easily prepared with reference to, for example, a method represented by the following Reaction Formula 1:

[Reaction Formula 1]

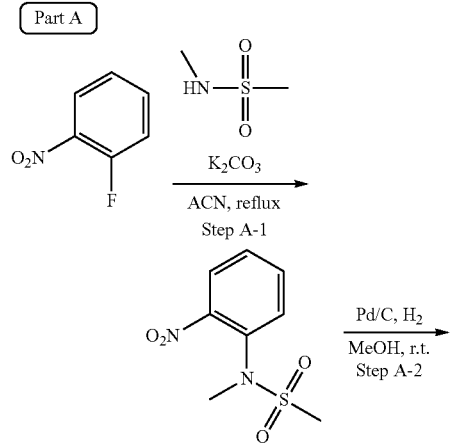

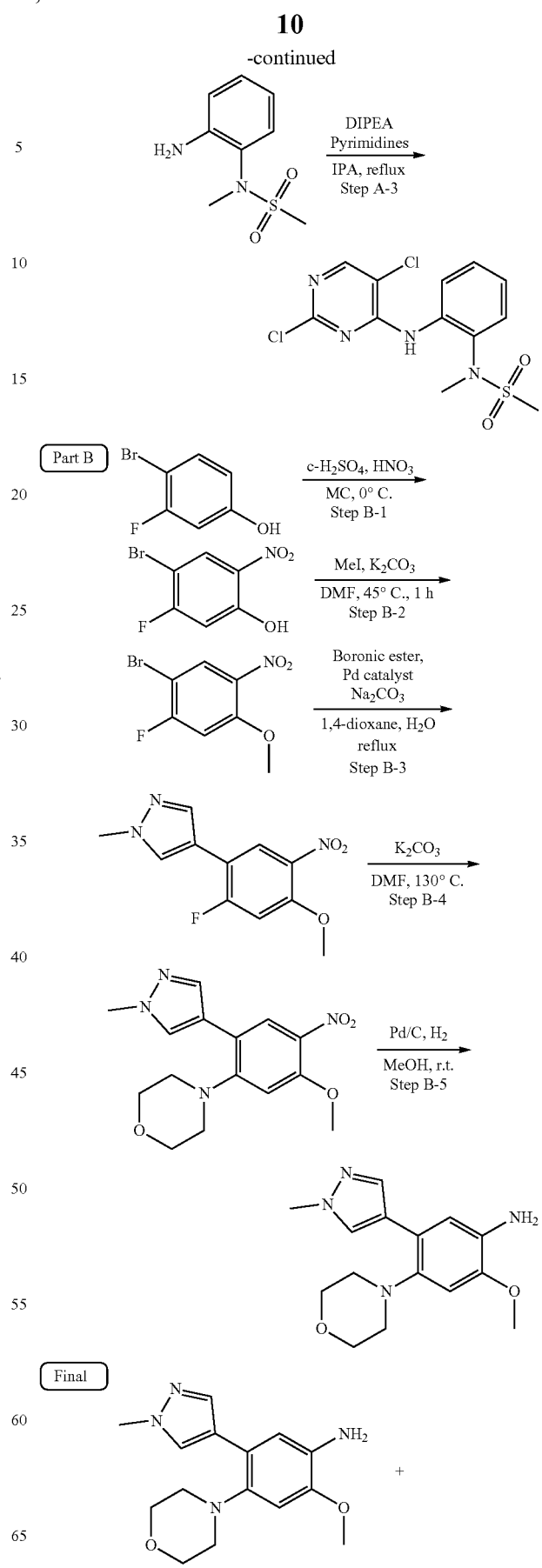

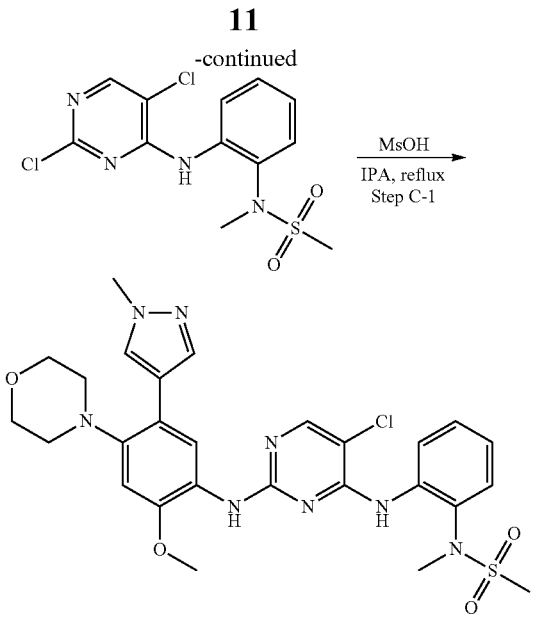

Synthesis Example 1. Synthesis of N-(2-((5-chloro-2-((2-methoxy-5-(1-methyl-1H-pyrazol-4-yl)-4-morpholinophenyl)amino)pyrimidine-4-yl)amino)phenyl)-N-methylmethanesulfonamide Step A-1: Synthesis of N-methyl-N-(2-nitrophenyl)methanesulfonamide 1-fluoro-2-nitrobenzene (1.0 eq.) was dissolved in acetonitrile, and added with potassium carbonate (2.0 eq.) and N-methylmethanesulfonamide (1.4 eq.) at room temperature. Then, the mixture was stirred overnight at 80° C. After completion of the reaction, the temperature was lowered to room temperature and the mixture was filtered. A filtrate was evaporated under reduced pressure to obtain a compound. The compound was used in a next reaction without a separation process.

Step A-2: Synthesis of N-(2-aminophenyl)-N-methylmethanesulfonamide

N-methyl-N-(2-nitrophenyl)methanesulfonamide (1.0 eq.) was dissolved in methanol and ethyl acetate (1:1) and added with 10% palladium/charcoal (0.2 eq.). The mixture was stirred for 2 hours under hydrogen. After completion of the reaction, the mixture was filtered using celite. A filtrate was evaporated under reduced pressure. The mixture was solidified using ethyl ether and penthane. The mixture was filtered to obtain a target compound. The compound was used in a next reaction without a separation process.

Step A-3: Synthesis of N-(2-((2,5-dichloropyrimidine-4-yl)amino)phenyl)-N-methylmethanesulfonamide N-(2-aminophenyl)-N-methylmethanesulfonamide (1.0 eq.) was dissolved in isopropyl alcohol and added with 2,4,5-trichloropyrimidine (1.1 eq.) and N, N-diisopropyl ethyl amine (2.5 eq.) at room temperature. The mixture was stirred overnight at 80° C. After completion of the reaction, the mixture was evaporated under reduced pressure and extracted using water and dichloromethane. An organic layer was washed using 2N hydrochloric acid. The organic layer was evaporated under reduced pressure to obtain a target compound. The compound was used in a next reaction without a separation process.

Step B-1: Synthesis of 4-bromo-5-fluoro-2-nitrophenol 4-bromo-3-fluorophenol was dissolved in dichloromethane. Strong sulfuric acid and nitric acid were added at 0° C. The mixture was stirred for 2 hours at the same temperature. After completion of the reaction, the mixture was neutralized using sodium bicarbonate saturated in water. The mixture was extracted with dichloromethane. An organic layer was collected and evaporated under reduced pressure to obtain a target compound. The compound was used in a next reaction without a separation process.

Step B-2: Synthesis of 1-bromo-2-fluoro-4-methoxy-5-nitrobenzene 4-bromo-5-fluoro-2-nitrophenol (1.0 eq.) was dissolved in N, N-dimethylformamide and added with potassium carbonate (2.0 eq.) and methyl iodide (1.5 eq.) at room temperature. The mixture was stirred for 2 hours at 45° C. After completion of the reaction, the mixture was extracted with water and ethyl acetate to collect an organic layer. The organic layer was evaporated under reduced pressure to obtain a target compound (hexane:ethyl acetate=10:1) by using column chromatography.

Step B-3: Synthesis of 4-(2-fluoro-4-methoxy-5-nitrophenyl)-1-methyl-1H-pyrazole 1-bromo-2-fluoro-4-methoxy-5-nitrobenzene (1.0 eq.) was dissolved in 1,4-dioxane and water, and 1-added with methylpyrazol-4-boronic acid pinacol ester (1.2 eq.), sodium carbonate (2.0 eq.), and a palladium catalyst (0.1 eq.) at room temperature. The mixture was refluxed and stirred overnight. After completion of the reaction, the mixture was extracted with water and ethyl acetate to collect an organic layer. The organic layer was evaporated under reduced pressure to obtain a target compound (hexane:ethyl acetate=5:1 to 3:1) by using column chromatography.

Step B-4: Synthesis of 4-(5-methoxy-2-(1-methyl-1H-pyrazol-4-yl)-4-nitrophenyl) morpholine 4-(2-fluoro-4-methoxy-5-nitrophenyl)-1-methyl-1H-pyrazole (1.0 eq.) was dissolved in N, N-dimethylformamide and added with potassium carbonate (1.2 eq.) and morpholine (1.2 eq.) at room temperature. The mixture was stirred overnight at 130° C. After completion of the reaction, the mixture was extracted with water and ethyl acetate to collect an organic layer. The organic layer was evaporated under reduced pressure to obtain a target compound (hexane:ethyl acetate=1:1 to 1:2) by using column chromatography.

Step B-5: Synthesis of 2-methoxy-5-(1-methyl-1H-pyrazol-4-yl)-4-morpholinoaniline 4-(5-methoxy-2-(1-methyl-1H-pyrazol-4-yl)-4-nitrophenyl) morpholine (1.0 eq.) was dissolved in methyl alcohol and ethyl acetate (1:1) and added with 10% palladium/charcoal (0.2 eq.). The mixture was stirred for 2 hours under hydrogen. After completion of the reaction, the mixture was filtered using celite. A filtrate was evaporated under reduced pressure. The mixture was solidified using hexane and the made solid was used to a next reaction without a separation process.

Step C-1: Synthesis of Final Compound

A pyrimidine derivative (1.0 eq.) was dissolved in isopropyl alcohol and added with an aniline derivative (1.0 eq.) and methanesulfoninate (1.3 eq.) at room temperature. The mixture was stirred overnight at 80° C. After completion of the reaction, the mixture was evaporated under reduced pressure to remove a solvent and using extracted water a 10% and methanol/dichloromethane mixture solution. An organic layer was evaporated under reduced pressure to obtain a target compound using column chromatography (10% methyl alcohol/dichloromethane).

Example 1: N-(2-((5-chloro-2-((2-methoxy-5-(1-methyl-1H-pyrazol-4-yl)-4-morpholinophenyl)amino)pyrimidine-4-yl)amino)phenyl)-N-methyl-methanesulfonamide (Chemical Formula 1)

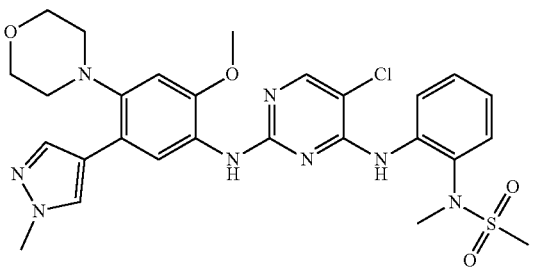 [SMILES: COc1cc(N2CCOCC2)c(-c2cnn(C)c2)cc1Nc1ncc(Cl)c(Nc2ccccc2N(C)S(C)(=O)=O)n1]

A final compound was prepared by the above method.
Yield: 69.5%, White solid,
$^1$H NMR (400 MHZ, DMSO-d6) δ 8.25 (d, J=2.4 Hz, 2H), 8.16 (d, J=8.6 Hz, 1H), 8.10 (s, 1H), 8.00 (s, 1H), 7.79 (d, J=0.8 Hz, 1H), 7.56 (s, 1H), 7.52 (dd, J=8.0, 1.5 Hz, 1H), 7.02 (t, J=7.6 Hz, 1H), 6.83 (bs, 1H), 6.76 (s, 1H), 3.80 (s, 3H), 3.76 (s, 3H), 3.70 (m, 4H), 3.14 (s, 3H), 3.05 (s, 3H), 2.80 (m, 4H). MS: ESI m/z 599.04 [M+H]+

Example 2: N-(2-((5-chloro-2-((2-methoxy-5-(1-methyl-1H-pyrazol-4-yl)-4-morpholinophenyl)amino)pyrimidine-4-yl)amino)phenyl)methanesulfonamide (Chemical Formula 2)

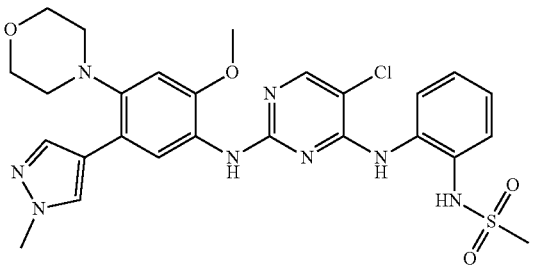 [SMILES: COc1cc(N2CCOCC2)c(-c2cnn(C)c2)cc1Nc1ncc(Cl)c(Nc2ccccc2NS(C)(=O)=O)n1]

In Step A-1, the compound was synthesized using methanesulfonamide.
Yield: 62.6%, White solid,
$^1$H NMR (400 MHZ, DMSO-d6) δ 9.26 (s, 1H), 8.42 (s, 1H), 8.08 (d, J=1.8 Hz, 2H), 7.98-7.87 (m, 2H), 7.77 (d, J=0.8 Hz, 1H), 7.56 (s, 1H), 7.26 (dd, J=8.0, 1.5 Hz, 1H), 6.99 (t, J=7.6 Hz, 1H), 6.80 (s, 1H), 6.73 (s, 1H), 3.80 (s, 3H), 3.75 (s, 3H), 3.68 (m, 4H), 2.92 (s, 3H), 2.83-2.72 (m, 4H). MS: ESI m/z 585.05 [M+H]+

Example 3: N-(2-((5-chloro-2-((2-methoxy-5-(1-methyl-1H-pyrazol-4-yl)-4-thiomorpholinophenyl)amino)pyrimidine-4-yl)amino)phenyl)-N-methoxymethanesulfonamide (Chemical Formula 3)

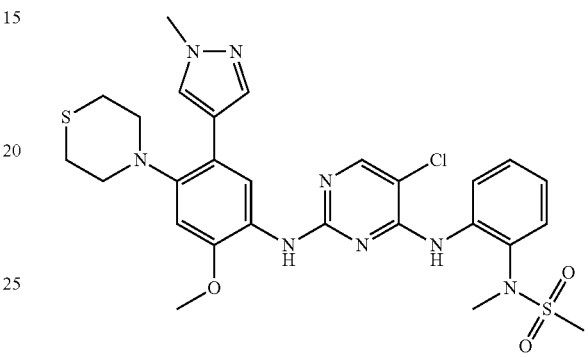

In Step B-4, the compound was synthesized using thiomorpholine.
Yield: 58.9%, White solid,
$^1$H NMR (400 MHZ, DMSO-d6) δ 8.26 (d, J=2.4 Hz, 2H), 8.14 (d, J=8.6 Hz, 1H), 8.09 (s, 1H), 8.01 (s, 1H), 7.79 (d, J=0.8 Hz, 1H), 7.56 (s, 1H), 7.52 (dd, J=8.0, 1.5 Hz, 1H), 7.02 (t, J=7.6 Hz, 1H), 6.83 (bs, 1H), 6.76 (s, 1H), 3.94 (s, 3H), 3.86 (s, 3H), 3.72 (m, 4H), 3.33 (d, J=12.0 Hz, 5H), 2.95 (m, 4H). MS: ESI m/z 615.04 [M+H]+

Example 4: N-(2-((5-chloro-2-((2-methoxy-5-(1-methyl-1H-pyrazol-4-yl)-4-(4-methylpiperazine-1-yl)phenyl)amino)pyrimidine-4-yl)amino)phenyl)-N-methoxymethanesulfonamide (Chemical Formula 4)

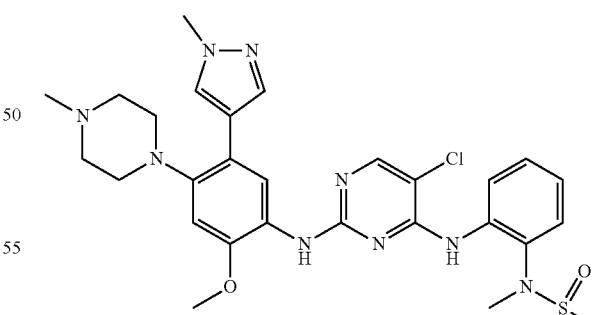

In Step B-4, the compound was synthesized using N-methylpiperazine.
Yield: 61.5%, Off-white solid,
$^1$H NMR (400 MHZ, DMSO-d6) δ 8.24 (d, J=2.4 Hz, 2H), 8.13 (d, J=8.6 Hz, 1H), 8.11 (s, 1H), 7.98 (s, 1H), 7.77 (d, J=0.8 Hz, 1H), 7.53 (s, 1H), 7.51 (dd, J=8.0, 1.5 Hz, 1H), 7.02 (t, J=7.6 Hz, 1H), 6.83 (bs, 1H), 6.76 (s, 1H), 3.94 (s, 3H), 3.87 (s, 3H), 3.42-3.25 (m, 11H), 3.19-3.07 (m, 2H), 2.96 (m, 2H), 2.26 (s, 3H). MS: ESI m/z 612.02 [M+H]+

Example 5: N-(2-((5-chloro-2-((2-methoxy-5-(1-methyl-1H-pyrazol-4-yl)-4-(2-oxa-6-azaspiro[3.3]heptane-6-yl)phenyl)amino)pyrimidine-4-yl)amino)phenyl)-N-methylmethanesulfonamide (Chemical Formula 5)

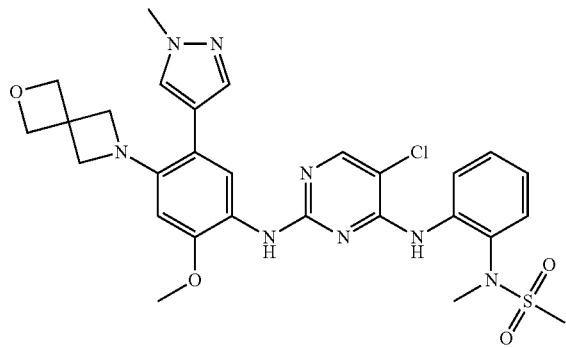 [SMILES: COc1cc(N2CC3(COC3)C2)c(-c2cnn(C)c2)cc1Nc1ncc(Cl)c(Nc2ccccc2N(C)S(C)(=O)=O)n1]

In Step B-4, the compound was synthesized using 2-oxa-6-azaspiro[3.3]heptane.
Yield: 45.3%, White solid,
$^1$H NMR (400 MHZ, DMSO-d6) δ 8.28 (d, J=2.4 Hz, 2H), 8.14 (d, J=8.6 Hz, 1H), 8.12 (s, 1H), 8.02 (s, 1H), 7.81 (bs, 1H), 7.57 (s, 1H), 7.54 (m, 1H), 7.02 (t, J=7.6 Hz, 1H), 6.83 (bs, 1H), 6.76 (s, 1H), 4.61 (s, 4H), 3.94 (s, 3H), 3.87 (s, 3H), 3.59 (s, 4H), 3.32 (s, 3H), 3.31 (s, 3H). MS: ESI m/z 611.09 [M+H]+

Example 6: N-(2-((5-chloro-2-((2-methoxy-5-(1-methyl-1H-pyrazol-4-yl)-4-(6-methyl-2,6-diazaspiro[3.3]heptane-2-yl)phenyl)amino)pyrimidine-4-yl)amino)phenyl)-N-methylmethanesulfonamide (Chemical Formula 6)

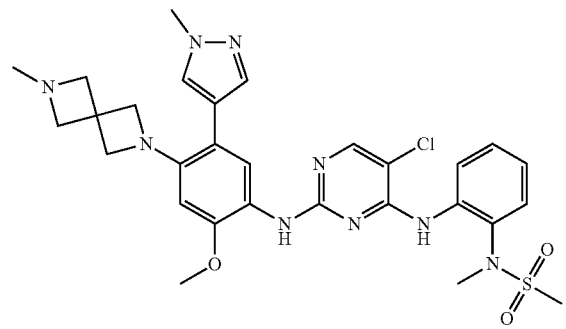

In Step B-4, the compound was synthesized using 2-methyl-2,6-diazaspiro[3.3]heptane.
Yield: 40.1%, Off-white solid,
$^1$H NMR (400 MHZ, DMSO-d6) δ 8.28 (d, J=2.4 Hz, 2H), 8.17 (d, J=8.6 Hz, 1H), 8.13 (s, 1H), 8.02 (s, 1H), 7.81 (d, J=0.8 Hz, 1H), 7.55 (s, 1H), 7.52 (dd, J=8.0, 1.5 Hz, 1H), 7.02 (t, J=7.6 Hz, 1H), 6.83 (bs, 1H), 6.76 (s, 1H), 3.94 (s, 3H), 3.87 (s, 3H), 3.59 (s, 4H), 3.35 (s, 3H), 3.33 (s, 3H), 3.22 (s, 4H), 2.12 (s, 3H). MS: ESI m/z 624.08 [M+H]+

Example 7: N-(2-((5-chloro-2-((2-methoxy-5-(1-methyl-1H-pyrazol-4-yl)-4-thiomorpholinophenyl)amino)pyrimidine-4-yl)amino)phenyl)methanesulfonamide (Chemical Formula 7)

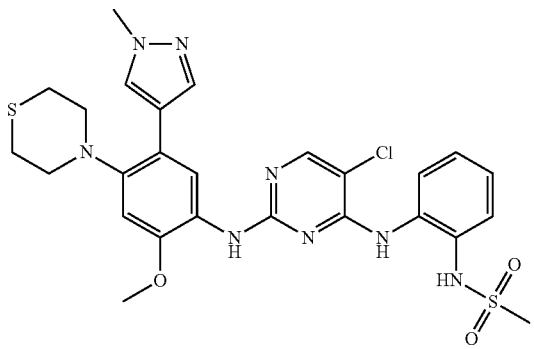 [SMILES: COc1cc(N2CCSCC2)c(-c2cnn(C)c2)cc1Nc1ncc(Cl)c(Nc2ccccc2NS(C)(=O)=O)n1]

In step B-4, the compound was synthesized using N-methanesulfonamide and thiomorpholine.
Yield: 53.6%, Off-white solid, 1H NMR (400 MHZ, DMSO-d6) δ 9.25 (s, 1H), 8.40 (s, 1H), 8.06 (d, J=1.8 Hz, 2H), 7.96-7.85 (m, 2H), 7.73 (d, J=0.8 Hz, 1H), 7.55 (s, 1H), 7.22 (dd, J=8.0, 1.5 Hz, 1H), 6.96 (t, J=7.6 Hz, 1H), 6.78 (s, 1H), 6.71 (s, 1H), 3.94 (s, 3H), 3.87 (s, 3H), 3.72 (m, 4H), 3.10 (m, 4H), 2.90 (s, 3H). MS: ESI m/z 601.02 [M+H]+

Example 8: N-(2-((5-chloro-2-((2-methoxy-5-(1-methyl-1H-pyrazol-4-yl)-4-(4-methylpiperazine-1-yl)phenyl)amino)pyrimidine-4-yl)amino)phenyl)methanesulfonamide (Chemical Formula 8)

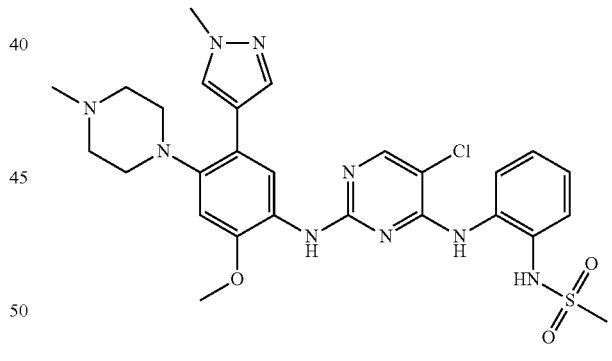

In step B-4, the compound was synthesized using N-methanesulfonamide and N-methylpiperazine.
Yield: 63.4%, White solid,
$^1$H NMR (400 MHZ, DMSO-d6) δ 9.29 (s, 1H), 8.49 (s, 1H), 8.02-7.87 (m, 4H), 7.77 (d, J=0.8 Hz, 1H), 7.56 (s, 1H), 7.26 (dd, J=8.0, 1.5 Hz, 1H), 7.00 (t, J=7.6 Hz, 1H), 6.83 (s, 1H), 6.73 (s, 1H), 3.94 (s, 3H), 3.87 (s, 3H), 3.42-3.25 (m, 5H), 3.19-3.07 (m, 2H), 2.96 (m, 2H), 2.90 (s, 3H), 2.16 (s, 3H). MS: ESI m/z 598.01 [M+H]+

Example 9: N-(2-((5-chloro-2-((2-methoxy-5-(1-methyl-1H-pyrazol-4-yl)-4-(2-oxa-6-azaspiro[3.3]heptane-6-yl)phenyl)amino)pyrimidine-4-yl)amino)phenyl)methanesulfonamide (Chemical Formula 9)

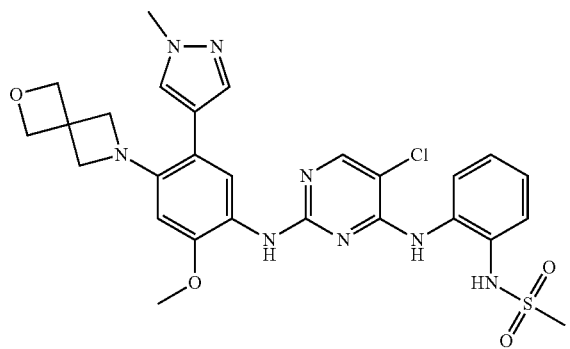 [SMILES: COc1cc(N2CC3(COC3)C2)c(-c2cnn(C)c2)cc1Nc1ncc(Cl)c(Nc2ccccc2NS(C)(=O)=O)n1]

In Step B-4, the compound was synthesized using N-methanesulfonamide and 2-oxa-6-azaspiro[3.3]heptane.
Yield: 40.1%, White solid,
$^1$H NMR (400 MHZ, DMSO-d6) δ 9.25 (s, 1H), 8.40 (s, 1H), 8.07 (d, J=1.8 Hz, 2H), 7.97-7.89 (m, 2H), 7.75 (d, J=0.8 Hz, 1H), 7.54 (s, 1H), 7.23 (dd, J=8.0, 1.5 Hz, 1H), 6.98 (t, J=7.6 Hz, 1H), 6.81 (s, 1H), 6.71 (s, 1H), 4.61 (s, 4H), 3.94 (s, 3H), 3.87 (s, 3H), 3.59 (s, 4H), 2.90 (s, 3H). MS: ESI m/z 597.03 [M+H]+

Example 10: N-(2-((5-chloro-2-((2-methoxy-5-(1-methyl-1H-pyrazol-4-yl)-4-(6-methyl-2,6-diazaspiro[3.3]heptane-2-yl)phenyl)amino)pyrimidine-4-yl)amino)phenyl)methanesulfonamide (Chemical Formula 10)

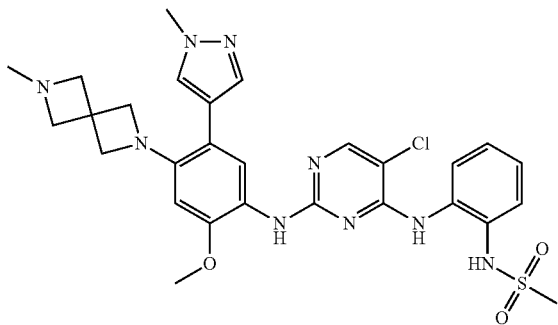

In Step B-4, the compound was synthesized using N-methanesulfonamide and 2-methyl-2,6-diazaspiro[3.3]heptane.
Yield: 37.2%, Off-white solid,
$^1$H NMR (400 MHZ, DMSO-d6) δ 9.46 (s, 1H), 8.82 (s, 1H), 8.28 (m, 2H), 7.94-7.82 (m, 2H), 7.70 (d, J=0.8 Hz, 1H), 7.53 (s, 1H), 7.22 (dd, J=8.0, 1.5 Hz, 1H), 6.94 (t, J=7.6 Hz, 1H), 6.81 (s, 1H), 6.70 (s, 1H), 3.94 (s, 3H), 3.87 (s, 3H), 3.59 (s, 4H), 3.22 (s, 4H), 2.92 (s, 3H), 2.15 (s, 3H). MS: ESI m/z 610.08 [M+H]+

Experimental Example 1: Measurement of Kinase Inhibitory Activity

With respect to the compounds of Example 1, kinase inhibitory activity including an ALK mutation and an EGFR mutation was measured and the result thereof was shown in Table 1 below. The measurement of the kinase inhibitory activity was performed in the following method. Each compound calculated a $IC_{50}$ value at a concentration in which the kinase inhibitory activity was inhibited, and the result thereof was shown as A, B, C, and D in Table 1 below. Here, A means $IC_{50} \leq 50$ nM, B means $IC_{50}$ 50 to 100 nM, and C means $IC_{50} > 100$ nM. As a contrast drug, crizotinib, alectinib, and osimertinib were used, respectively.

1. Each kinase was cultured under 8 mM MOPS, pH 7.0, 0.2 mM EDTA, 250 µM KKKGQEEEYVFIE (SEQ ID NO: 1), 1 mM sodium orthovanadate, 5 mM sodium-6-glycerophosphate, 10 mM Magnesium acetate, and [n-33P]-ATP.
2. An evaluation compound (DMSO solution) and Mg/ATP were added to perform the reaction.
3. After about 40 minutes at room temperature, 10 µL of 0.5% phosphoric acid was added to complete the reaction.
4. The reaction solution was divided by 0.5% 10 µL and spotted on a P30 filtermat.
5. For about 4 minutes, the reaction solution was washed 4 times with 0.425% phosphoric acid. The reaction solution was washed once with methanol and then dried and analyzed with scintillation counting to measure $IC_{50}$ values.

TABLE 1

| Example | ALK (L1196M) | EGFR (del19/L858R/T790M) | EGFR (del19/T790M/C797S) |
|---|---|---|---|
| 1 | A | A | A |
| 2 | A | A | A |
| 3 | A | A | A |
| 4 | A | A | B |
| 5 | A | A | A |
| 6 | A | A | B |
| 7 | A | A | A |
| 8 | A | B | B |
| 9 | A | A | A |
| 10 | A | B | B |
| Crizotinib | A | C | C |
| Alectinib | A | C | C |
| Osimertinib | B | A | C |

As shown in the experimental results of Table 1, it was confirmed that the compounds prepared by Examples of the present invention were very excellent in ALK and EGFR kinase inhibitory activity as compared to crizotinib, alectinib, and osimertinib.

That is, unlike crizotinib, alectinib, and osimertinib targeting ALK and EGFR alone in the related art, respectively, it was confirmed that the compounds of the present invention were target therapeutic agents capable of targeting simultaneously ALK and EGFR and inhibited a C797S EGFR mutation protein showing resistance to osimertinib to have a very excellent effect.

Experimental Example 2: Measurement of Cancer Cell Growth Inhibitory Effect

With respect to the compounds obtained in Examples, a growth inhibitory effect of ALK mutation cancer cells and EGFR mutation Ba/F3 cancer cell lines was measured. The anti-cancer efficacy activity measurement was performed by the following method using an ALK mutation cell line such as H3122 (EML4-ALK v1), H2228 (EML4-ALK v3), etc. and an EGFR mutation Ba/F3 stable cell line.

Gene construction: Wild type and mutant EGFRs were purchased from Addgene (wild type, #11011; L858R, #11012; L858R+T790M, #32073; del19, #32062; del19+

T790M, #32072). All constructions have finally completed a viral particle for infection as a retroviral vector.

Ba/F3 stable cell line construction: Murine lymphoid cells performed IL-3 dependent growth. In this cell line, when each mutant EGFR construction was infected, oncogenic addiction was performed by the expression of mutant EGFR, and thus cells lived even without IL-3. A stable cell line was constructed using this principle even without puromycin selection. Briefly, each construction was infected on Ba/F3, and after 48 hours, IL-3 was removed by media exchange and cells were cultured. However, in the case of the wild type EGFR, puromycin selection was performed.

<Confirmation of Ba/F3 Stable Cell Line>

All stable cell lines performed western blotting to confirm the expression and EGFR activity of each construction (EGFR wild type and L858R were excluded).

<Confirmation (Western blotting) of Cellular Kinase Activity Change>

Drugs were treated to each stable cell line in a concentration dependent manner and the cells were obtained after 5 hours. Cell lysates were made using EBC lysis buffer (50 mM Tris-HCl [pH 8.0], 120 mM NaCl, 1% Triton X-100, 1 mM EDTA, 1 mM EGTA, 0.3 mM phenylmethylsulfonylfluoride, 0.2 mM sodium orthovanadate, 0.5% NP-40, and 5 U/mL aprotinin). The activity was measured using antibodies [p-EGFR (Tyr1173), EGFR, Akt, p-Erk, Erk, actin, from SantaCruz; p-Akt, from Cell signaling] of EGFR-related signaling molecules.

<Verification of anti-cancer effect through MTT assay>

$2\times10^5$ cells were seeded on a 96-well plate. After 24 hours, each of the drugs was treated in a dose dependent manner, and incubated after 72 hours, a 15 μL MTT reagent reacted for 4 hours, and then 100 μL 10% SDS was added and incubated for 24 hours. Changes in the final OD were read at 595 nm. MTT result analysis measured the $IC_{50}$ values through prism software.

The $IC_{50}$ value was calculated at a concentration of 50% inhibiting the cell growth by each compound, and the results were shown in Table 2 below. As a contrast drug, crizotinib, alectinib, and osimertinib were used, respectively. The results were shown as A, B, C, and D in Table 2 below. Here, A means $IC_{50} \leq 100$ nM, B means $IC_{50}$ 50 to 100 nM, and C means $IC_{50} > 500$ nM.

TABLE 2

| Example | H3122 | H2228 | DEL19/T790M/C797S |
|---|---|---|---|
| 1 | B | A | A |
| 2 | B | A | A |
| 3 | B | A | A |
| 4 | B | B | B |
| 5 | B | A | A |
| 6 | B | B | B |
| 7 | B | A | A |
| 8 | C | C | B |
| 9 | B | B | A |
| 10 | C | C | B |
| Crizotinib | B | B | C |
| Alectinib | B | B | C |
| Osimertinib | C | C | C |

As shown in the experimental result of Table 2 below, it was confirmed that the compounds prepared by Examples of the present invention exhibited a significantly inhibitory activity as compared with crizotinib, alectinib, and osimertinib with respect to a mutation expression cancer cell line.

Like the in vitro kinase assay result of Experimental Example 1, the compounds of the present invention were target therapeutic agents capable of targeting simultaneously ALK and EGFR and induced the death of cancer cells expressing a C797S EGFR mutation protein showing resistance to osimertinib to have a very excellent effect.

The invention claimed is:

1. A compound of Chemical Formula 1 below or a salt thereof:

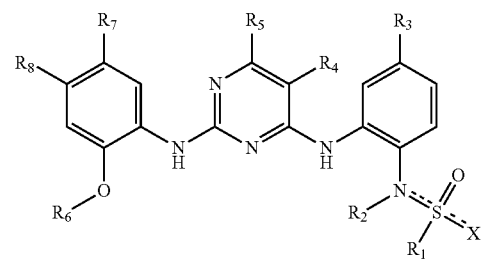

[Chemical Formula 1]

X is oxygen, $R_1$ is an alkyl group of C1 to C4, or a cycloalkyl group of C3 to C6, $R_2$ is H or an alkyl group of C1 to C4, $R_3$ is hydrogen or a halogen group, $R_4$ is hydrogen, a halogen group, or an alkyl group of C1 to C4, $R_5$ is hydrogen or an alkyl group of C1 to C4, $R_6$ is hydrogen or an alkyl group of C1 to C4, R$_7$ is a pyrazolyl group unsubstituted or substituted with a C1 to C4 alkyl group, an imidazolyl group unsubstituted or substituted with a C1 to C4 alkyl group, or a triazolyl group unsubstituted or substituted with a C1 to C4 alkyl group, and R$_8$ is a morpholinyl group unsubstituted or substituted with a C1 to C4 alkyl group, a thiomorpholinyl group unsubstituted or substituted with a C1 to C4 alkyl group, piperazinyl group unsubstituted or substituted with a C1 to C4 alkyl group, a diazaspiro group of C5 to C10 unsubstituted or substituted with a C1 to C4 alkyl group, an oxoazaspiro group of C5 to C10 unsubstituted or substituted with a C1 to C4 alkyl group, a thioazaspiro group of C5 to C10 unsubstituted or substituted with a C1 to C4 alkyl group, or a N$^1$,N$^1$,N$^2$-tri (C1 to C4 alkyl)ethylene diamine group, wherein X forms a double bond with S, and S forms a single bond with N.

2. The compound of Chemical Formula 1 or the salt thereof of claim 1, wherein the R$_7$ is selected from the following groups, and

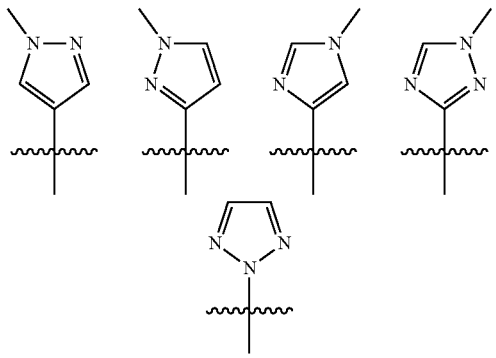

the R$_8$ is selected from the following groups:

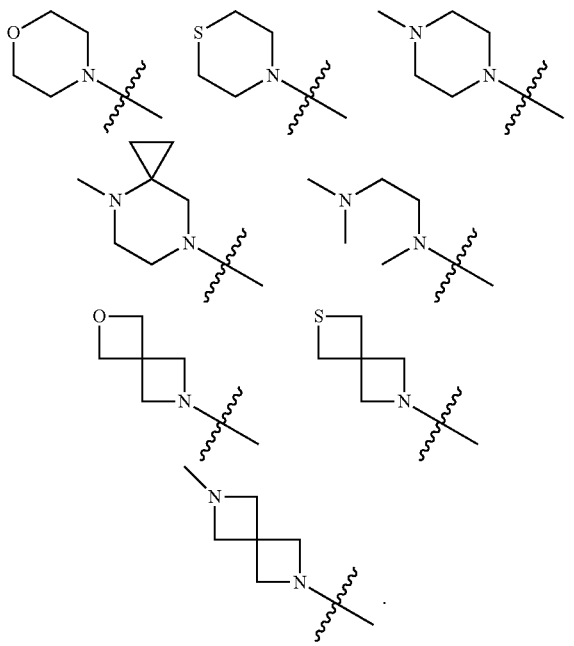

3. The compound of Chemical Formula 1 or the salt thereof of claim 1, wherein
X is oxygen,
R$_1$ is an alkyl group of C1 to C4,
R$_2$ is H or an alkyl group of C1 to C4,
R$_3$ is hydrogen or a halogen group,
R$_4$ is hydrogen or a halogen group,
R$_5$ is hydrogen or an alkyl group of C1 to C4,
R$_6$ is an alkyl group of C1 to C4,
R$_7$ is selected from the following groups, and

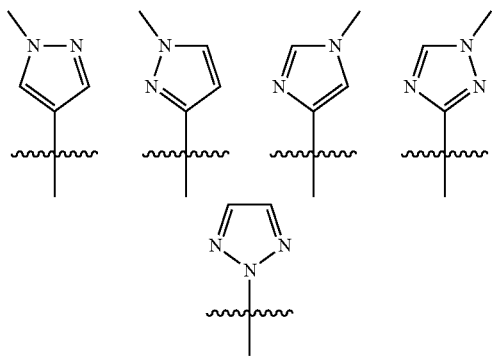

R$_8$ is selected from the following groups:

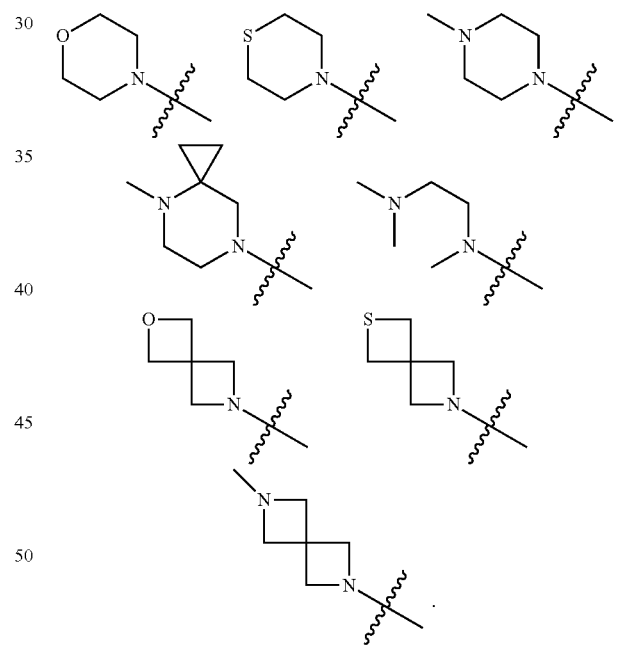

4. The compound of Chemical Formula 1 or the salt thereof of claim 1, wherein
the compound of Chemical Formula 1 is selected from the following compounds:
N-(2-((5-chloro-2-((2-methoxy-5-(1-methyl-1H-pyrazol-4-yl)-4-morpholinophenyl)amino)pyrimidine-4-yl)amino)phenyl)-N-methylmethanesulfonamide,
N-(2-((5-chloro-2-((2-methoxy-5-(1-methyl-1H-pyrazol-4-yl)-4-morpholinophenyl)amino)pyrimidine-4-yl)amino)phenyl)methanesulfonamide,
N-(2-((5-chloro-2-((2-methoxy-5-(1-methyl-1H-pyrazol-4-yl)-4-thiomorpholinophenyl)amino)pyrimidine-4-yl)amino)phenyl)-N-methoxymethanesulfonamide, N-(2-((5-chloro-2-((2-methoxy-5-(1-methyl-1H-pyrazol-4-yl)-4-(4-methylpiperazine-1-yl)phenyl)amino)pyrimidine-4-yl)amino)phenyl)-N-methoxymethanesulfonamide,
N-(2-((5-chloro-2-((2-methoxy-5-(1-methyl-1H-pyrazol-4-yl)-4-(2-oxa-6-azaspiro[3.3]heptane-6-yl)phenyl)amino)pyrimidine-4-yl)amino)phenyl)-N-methylmethanesulfonamide,
N-(2-((5-chloro-2-((2-methoxy-5-(1-methyl-1H-pyrazol-4-yl)-4-(6-methyl-2,6-diazaspiro[3.3]heptane-2-yl)phenyl)amino)pyrimidine-4-yl)amino)phenyl)-N-methylmethanesulfonamide,
N-(2-((5-chloro-2-((2-methoxy-5-(1-methyl-1H-pyrazol-4-yl)-4-thiomorpholinophenyl)amino)pyrimidine-4-yl)amino)phenyl)methanesulfonamide,
N-(2-((5-chloro-2-((2-methoxy-5-(1-methyl-1H-pyrazol-4-yl)-4-(4-methylpiperazine-1-yl)phenyl)amino)pyrimidine-4-yl)amino)phenyl)methanesulfonamide,
N-(2-((5-chloro-2-((2-methoxy-5-(1-methyl-1H-pyrazol-4-yl)-4-(2-oxa-6-azaspiro[3.3]heptane-6-yl)phenyl)amino)pyrimidine-4-yl)amino)phenyl)methanesulfonamide, and
N-(2-((5-chloro-2-((2-methoxy-5-(1-methyl-1H-pyrazol-4-yl)-4-(6-methyl-2,6-diazaspiro[3.3]heptane-2-yl)phenyl)amino)pyrimidine-4-yl)amino)phenyl)methanesulfonamide.

5. The compound of Chemical Formula 1 or the salt thereof of claim 1, wherein
the salt is a salt of an acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, benzoic acid, hydroxybenzoic acid, phenyl acetic acid, cinnamic acid, salicylic acid, methanesulfonic acid, ethanesulfonic acid, benzene sulfonic acid, and toluene sulfonic acid.

6. A pharmaceutical composition comprising the compound of claim 1 or a pharmaceutically acceptable salt thereof, as an active ingredient, and a pharmaceutically acceptable carrier.

7. A method for treating lung cancer in a subject in need thereof, comprising administering an effective amount of the compound of claim 1 or a pharmaceutically acceptable salt thereof to the subject.

8. The method of claim 7, wherein
the lung cancer is anaplastic lymphoma kinase (ALK) mutation and epidermal growth factor receptor (EGFR) expression lung cancer.

* * * * *